(12) United States Patent
Takezawa et al.

(10) Patent No.: US 7,195,912 B2
(45) Date of Patent: Mar. 27, 2007

(54) HYDROGEL THIN FILM CONTAINING EXTRACELLULAR MATRIX COMPONENTS

(75) Inventors: Toshiaki Takezawa, Hyogo (JP); Katsutoshi Yoshizato, Hiroshima (JP)

(73) Assignee: Japan Science and Technology Corporation, Saitama (JP)

( * ) Notice: Subject to any disclaimer, the term of this patent is extended or adjusted under 35 U.S.C. 154(b) by 0 days.

(21) Appl. No.: 11/035,954

(22) Filed: Jan. 18, 2005

(65) Prior Publication Data

US 2005/0129720 A1 Jun. 16, 2005

Related U.S. Application Data

(60) Division of application No. 10/419,932, filed on Apr. 22, 2003, which is a continuation of application No. 10/084,426, filed on Feb. 28, 2002, now abandoned, which is a continuation of application No. 08/925,682, filed on Sep. 9, 1997, now abandoned.

(51) Int. Cl.
*C12N 5/00* (2006.01)
*C12N 5/02* (2006.01)

(52) U.S. Cl. .................... 435/397; 435/395

(58) Field of Classification Search .............. None
See application file for complete search history.

(56) References Cited

U.S. PATENT DOCUMENTS

| | | | |
|---|---|---|---|
| 4,388,428 A * | 6/1983 | Kuzma et al. ............. 523/106 |
| 4,570,629 A | 2/1986 | Widra ....................... 128/156 |
| 4,612,012 A | 9/1986 | White ............................ 623/5 |
| 4,983,181 A | 1/1991 | Civerchia ...................... 623/5 |
| 5,015,584 A * | 5/1991 | Brysk ........................ 424/93.7 |
| 5,106,743 A | 4/1992 | Franzblau et al. ....... 435/240.2 |
| 5,106,949 A * | 4/1992 | Kemp et al. ................ 530/356 |
| 5,108,428 A | 4/1992 | Capecchi et al. .............. 623/5 |
| 5,206,028 A | 4/1993 | Li ............................... 424/484 |
| 5,336,501 A | 8/1994 | Czech et al. ................ 424/445 |
| 5,374,515 A | 12/1994 | Parenteau et al. ............ 435/1 |
| 5,429,590 A * | 7/1995 | Saito et al. ................... 602/48 |
| 5,431,639 A * | 7/1995 | Shaw ........................ 604/264 |
| 5,536,656 A * | 7/1996 | Kemp et al. ................ 435/371 |
| 5,591,709 A | 1/1997 | Lindenbaum ................ 514/4 |
| 5,709,934 A * | 1/1998 | Bell et al. ................ 428/305.5 |
| 5,712,161 A * | 1/1998 | Koezuka et al. ............ 435/382 |
| 5,736,399 A * | 4/1998 | Takezawa et al. .......... 435/399 |
| 5,836,313 A * | 11/1998 | Perez et al. ................. 128/898 |

FOREIGN PATENT DOCUMENTS

| EP | 246013 | | 11/1987 |
|---|---|---|---|
| JP | 08163996 | * | 6/1996 |
| JP | 8228768 | | 9/1996 |

* cited by examiner

*Primary Examiner*—Christopher R. Tate
(74) *Attorney, Agent, or Firm*—Wenderoth, Lind & Ponack, L.L.P.

(57) ABSTRACT

The thin film of the invention comprises a hydrate of a vitrified gel containing one or more extracellular matrix components, which can be integrated with a retainer as required. A hydrogel thin film containing one or more extracellular matrix components such as thin-film collagen hydrogel thin film, which is useful for a cell culture substratum and for preventing organ adhesion, can be easily prepared, and is excellent in expediency.

8 Claims, 5 Drawing Sheets

HYDROGEL THIN FILM CONTAINING EXTRACELLULAR MATRIX COMPONENTS

This application is a divisional application of Ser. No. 10/419,932, filed Apr. 22, 2003, currently pending, which is a continuation of Ser. No. 10/084,426, filed Feb. 28, 2002, now abandoned, which is a continuation application of Ser. No. 08/925,682, filed Sep. 9, 1997, now abandoned.

BACKGROUND OF THE INVENTION

1. Field of the Invention

The present invention relates to a hydrogel thin film containing one or more extracellular matrix components. More particularly, the present invention relates to a novel hydrogel thin film containing one or more extracellular matrix components, which is useful for a cell culture substratum and prevention of organ adhesion, has an appropriate elastic strength, can be easily prepared and can be used simply.

2. Description of the Related Art

Cell culture has conventionally been carried out in various manners for various purposes including development of various medical techniques and various medical drugs.

A method using an extracellular matrix components such as collagen is known as a method for cell culture. In this method, in the case of collagen for example, various trial efforts have been made to ensure a three-dimensionality as closest as possible to forms of biological tissues or functional expression by alleviating restrictions imposed as a two-dimensional planar culture for ordinary cell culture.

Regarding the culturing methods using collagen or the like attracting the general attention as to usage thereof, however, in the case of collagen hydrogel for example, there is a problem of difficulty in handling the collagen hydrogel itself because of the softness. It is not therefore easy to prepare a cell culture substratum, and a more simple method for utilization has not as yet been established.

Under such circumstances, the present inventors have carried out studies from various points of view regarding utilization of an extracellular matrix components such as collagen. The object of these studies was to improve the conventional culturing method, and to achieve a method for using a new matrix substance, which would permit easier preparation of a cell culture substratum, be simply applicable, provide satisfactory performance as a culture substratum, and be applicable also for preventing organ adhesion.

SUMMARY OF THE INVENTION

As means to solve the foregoing problems, the present invention provides a hydrogel thin film containing one or more extracellular matrix components, which is a thin film comprising a hydrate of a vitrified matrix gel containing one or more extracellular matrix components.

The present invention also provides also embodiments wherein the hydrogel thin film contains more than one extracellular matrix components, wherein one of the extracellular matrix components is collagen, wherein the hydrogel thin film has one or more cell culture medium components, and wherein the thin film is integrated with a retainer. There are provided embodiments of the retainer, wherein the retainer is an annular or a mesh shape, wherein the retainer comprises one or more biological absorbing substances, and wherein the retainer has a circular opening which comprises a cylinder retaining and integrating the thin film.

The present invention also provides a glass-like substance of a dried gel containing one or more extracellular matrix components as a precursor of the foregoing hydrogel thin film containing one or more extracellular matrix components.

The present invention further provides, regarding the foregoing hydrogel thin film containing one or more extracellular matrix components, a method comprising the steps of preparing the gel from a solution containing one or more extracellular matrix components, drying the resultant gel for vitrification thereof, and hydrating the vitrified gel, and a method in which a hydrogel thin film containing one or more extracellular matrix components is used as the cell culture substratum.

The present invention further provides a method of culturing cells using the foregoing substratum.

Figure 1:
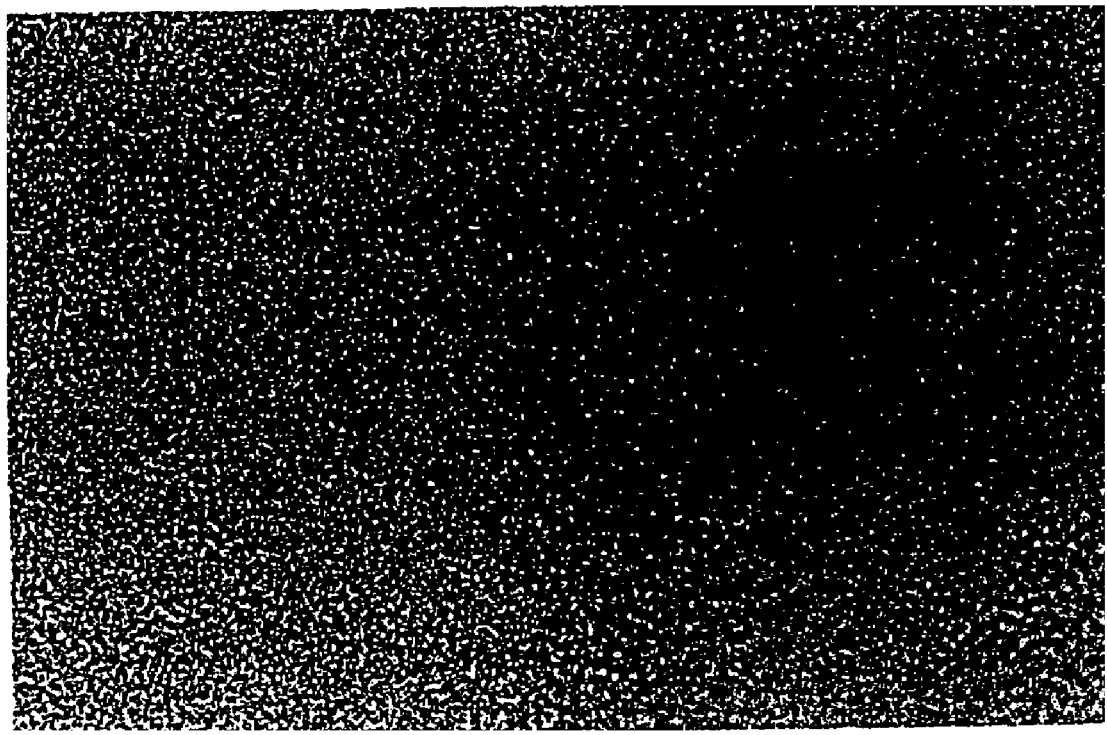
FIG. 1 shows a phase-contrast microphotograph illustrating the surface of a collagen hydrogel thin film as a reference.

In the drawings, the reference numerals represent the following components:
1: Circular wire retainer
10: Cylindrical appliance
11: Circular wire retainer
12: Collagen hydrogel thin film
13: Cover

DESCRIPTION OF THE PREFERRED EMBODIMENTS

As described above, the hydrogel thin film containing one or more extracellular matrix components of the present invention, as the thin film itself and as that integrated with the retainer, has an appropriate elastic strength and a thin film shape permitting easy handling, and enables achievement of a biochemical composition as a cell culture substratum, thus providing easy preparation for culturing and an excellent expediency.

Collagen is a representative extracellular matrix component and its application is attracting general attention. Applicable extracellular matrix components other than collagen include fibronectin, vitronectin, laminin, proteoglycan, glycosaminoglycan, and MATRIGEL (brand name), and may appropriately be used.

There is no particular restriction on the cell culture medium components, and optimum salt composition, concentration and pH are selected.

An annulus made of a wire or a metal line, or a mesh comprising gauze or other woven stuff may be appropriately used as a retainer. A biological absorbing substance may also be applicable. It suffices to select a shape, a size and a material in response to the manner of use. The retainer may be a cylinder having a circular opening, or a container as a precursor thereof.

Manufacture of a cell culture substratum comprises the steps of first mixing an aqueous solution of a matrix such as collagen with a composition having a medium or serum, placing any of various retainers as described above into this mixed solution, and incubating it at a suitable temperature for its gelation.

The resultant gel is vitrified by drying by air for example. This vitrification phenomenon, utilization of the thus vitrified gel after further modification, and use of the modified gel after vitrification as a cell culture substratum are not known, but disclosed for the first time in the present invention.

More particularly, in the manufacturing method of the present invention, the vitrified gel containing one or more extracellular matrix components such as collagen is hydrated. This provides a hydrogel thin film containing one or more extracellular matrix components having a satisfactory elastic strength, which serves as a cell culture substratum and is useful for preventing organ adhesion.

For vitrification, in the present invention, it is the general practice to slowly and completely dry the gel containing the extracellular matrix components having a terminal concentration in an aseptic manner (for example, through aseptic air drying), thereby vitrifying the gel. Hydration of the vitrified gel can easily be effected by treating it by PBS, for example.

The construction and the functions of the present invention will now be described below further in detail by means of examples involving collagen.

EXAMPLES

Example 1

Preparation of Collagen Hydrogel Thin Film:

2 ml of quintuple-concentration Dulbecco's Modified Eagle Medium (GIBCO #31600-034), 0.1 ml of 10,000 units/ml penicillin and 10,000 μg/ml streptomycin (GIBCO #15140-031), 0.2 ml of 1M HEPES (GIBCO #15630-023), 0.493 ml of 7.5% sodium bicarbonate solution (GIBCO #25080-011), 1.407 ml of distilled water, and 1 ml of fetal bovine serum were put in a sterilized conical tube (Falcon #2070) chilled on ice, having an inner volume of 50 ml, and mixed. Then 4.8 ml of 0.5% aqueous type-I collagen solution (CELLGEN I-AC or I-PC, made by Koken Company) was added into the tube and uniformly mixed. After placing 2 ml of the mixed collagen solution having a final concentration of 0.24% in a culture dish made of hydrophobic Polystyrene (ø35 mm; Falcon #1008), the solution was held in a humidified incubator at 37° C. in the presence of 5% $CO_2$/95% air in 3 hours for its gelation. This collagen gel of the final concentration of 0.24% was vitrified by completely air-drying slowly in an aseptic manner in the covered dish. The vitrified collagen gel was hydrated by adding 2 ml of PBS. The collagen gel thus hydrated was rinsed with 2 ml of PBS several times. The hydrated collagen gel was peeled off from the dish and collected by tracing the inner wall of the dish with a sharp-end pincette along the periphery, in the form of a thin-film collagen hydrogel having a satisfactory elastic strength, as shown in the phase-contrast microphotograph in FIG. 1.

Example 2

Figure 2:
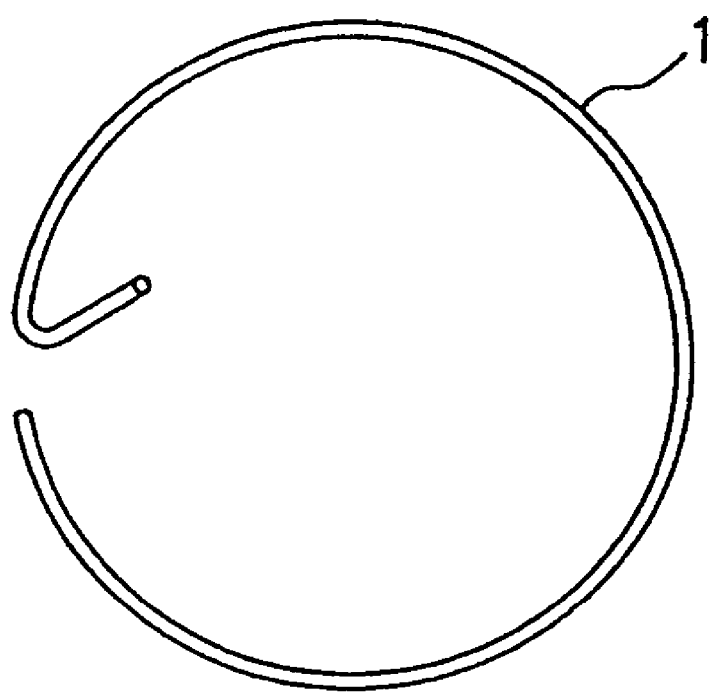
FIG. 2 shows a perspective view illustrating a circular wire serving as a retainer.
Figure 3:
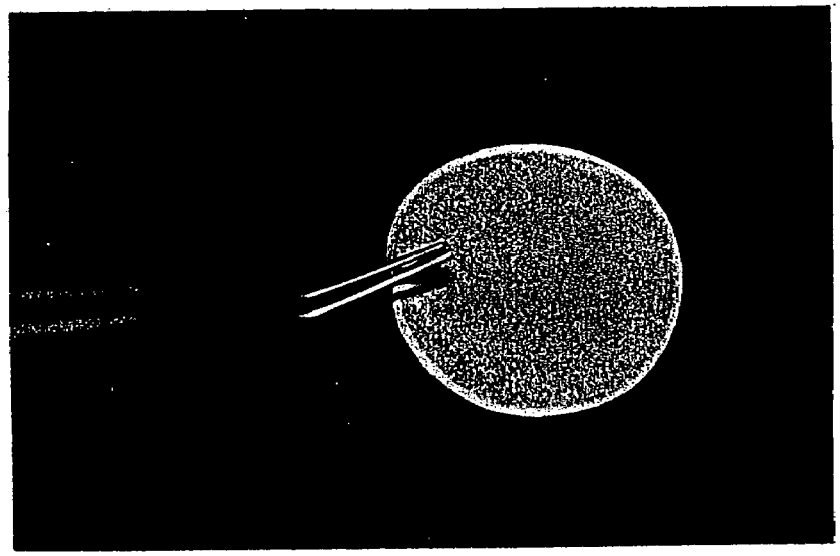
FIG. 3 shows a photograph showing a collagen hydrogel thin film substratum integrated with a circular wire retainer.

Preparation of Collagen Hydrogel Thin-Film with Peripheral Wire Retainer:

A circular retainer (1) with a knob as shown in FIG. 2 was made with a stainless steel wire (size: #20; 0.9 mm), and 2 ml of the mixed collagen solution having a final concentration of 0.24% prepared in Example 1 was placed, together with this wire retainer, into a hydrophobic polystyrene culture dish (ø35 mm; Falcon #1008). In the same manner as in Example 1, the colagen collagen solution with the retainer was vitrified after its gelation. The vitrified collagen gel was hydrated by adding 2 ml PBS. Further, the collagen gel thus hydrated was rinsed several times with 2 ml of PBS. The hydrated collagen gel could be peeled off and collected from the dish by slowly lifting the stainless steel knob, in the form of a thin-film collagen hydrogel having a satisfactory elastic strength with a wire retainer surrounding it as shown in FIG. 3.

Example 3

Preparation of Gauze Embedding Type Collagen Hydrogel Thin Film:

A sterilized type-III gauze as prescribed in the Japanese Pharmacopoeia (K-Pine made by, Kawamoto Hotai Zairyou Company) was cut in a circular shape with a knob in an aseptic manner, and immersed the cut gauze in a cell culture medium (Dulbecco's Modified Eagle Medium containing 10% fetal bovine serum, 20 mM HEPES, 100 units/ml penicillin and 100 μg/ml streptomycin). The gauze was put, together with 5 ml of the mixed collagen solution having a final concentration of 0.24% prepared in Example 1, in a hydrophobic polystyrene culture dish (ø60 mm; Falcon #1007). In the same manner as in example 1, the collagen solution with the gauze was vitrified after its gelation.

Figure 4:
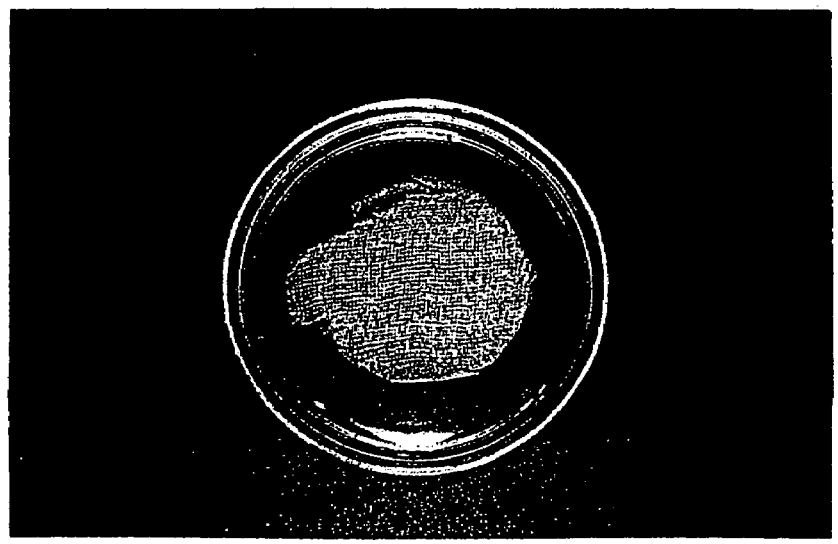
FIG. 4 shows a photograph showing a collagen hydrogel thin film embedded gauze.

Furthermore, the vitrified collagen gel was hydrated by adding PBS in the same manner as in Example 1. The hydrated collagen gel could be peeled off and collected from the dish by slowly lifting the knob of the gauze, in the form of a thin-film collagen hydrogel having a satisfactory elastic strength embedding the gauze as a whole as shown in FIG. 4.

Example 4

Figure 5:
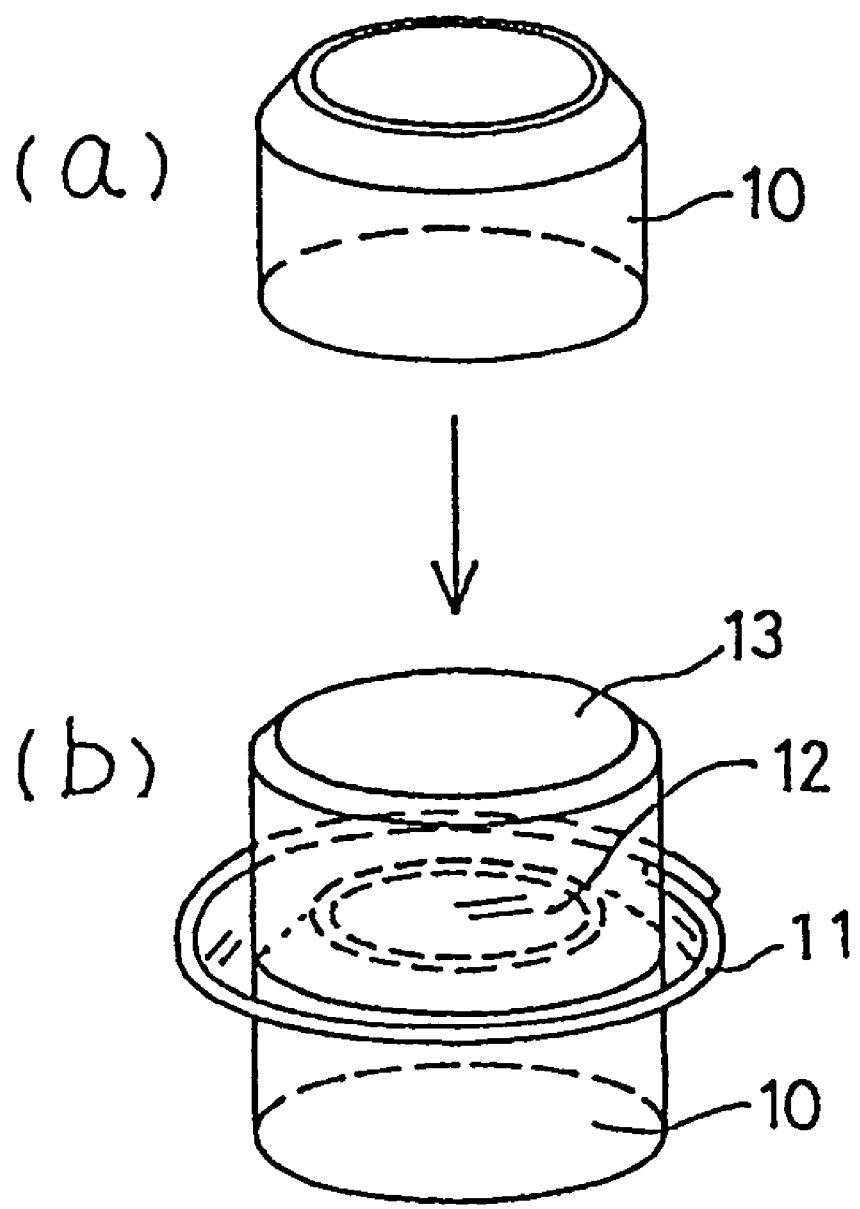
FIG. 5 shows a process diagram illustrating preparation of the substratum of the present invention using a cylinder as the retainer.

Preparation Cylinder-Retained Collagen Hydrogel Thin-Film:

A sterilized conical tube having an inner volume of 50 ml (Falcon #2070) was cut to prepare a cylindrical appliance (10) capable of fixing a collagen hydrogel thin-film as a cell culture substratum as shown in FIG. 5(a).

By the use of a collagen hydrogel thin film (12) with a wire peripheral retainer (11) prepared in Example 2, the cover (13) prepared from the conical tube was pressed as shown in FIG. 5(b), and then the wire retainer (11) was removed. By doing so, it was possible to transfer and fix easily the collagen hydrogel thin film onto an opening of the appliance (10). In this state, the resultant product could be used for cell culture. The gauze embedding type collagen hydrogel thin film shown in Example 3 could be fixed onto the appliance in the same manner as above.

Example 5

Figure 6:
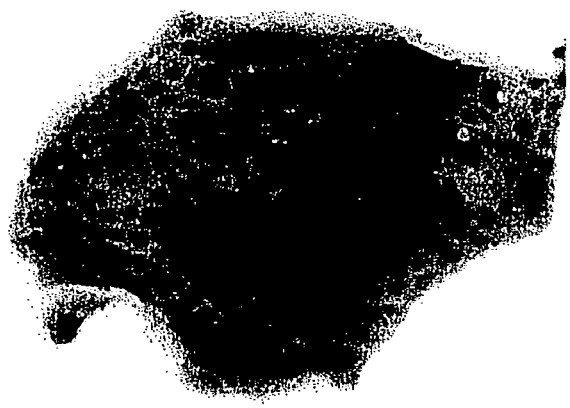
FIG. 6 shows a microphotograph showing formation of a colony for MEC.
Figure 7:
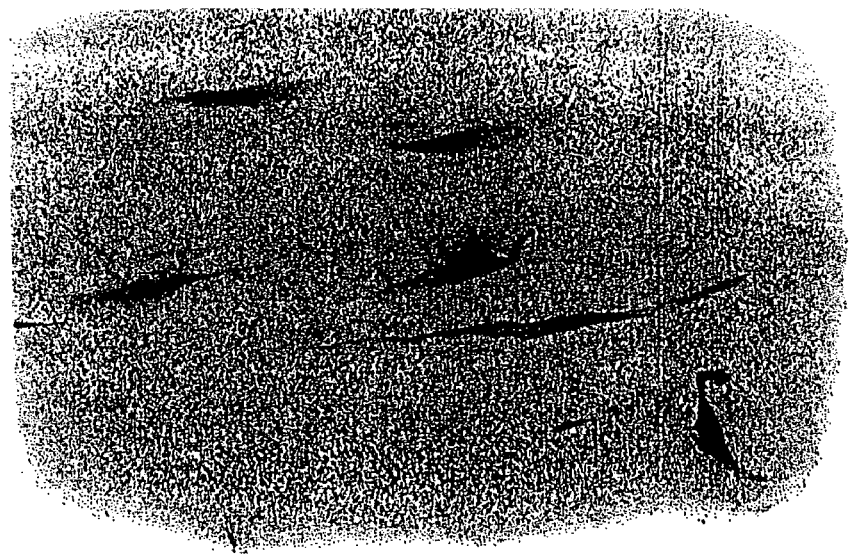
FIG. 7 shows a microphotograph showing the case of HDF.

Cell Culture on Collagen Hydrogel Thin Film:

10 ml of the cell culture medium was placed in a hydrophilic polystyrene culture dish (ø60 mm; Falcon #3002), and the collagen hydrogel fixed onto the appliance in Example 4 was put into the dish. 2 ml of the cell suspension ($3\times10^4$/ml) was seeded in the interior of the appliance and cultured in a humidified incubator at 37° C. in the presence of 5% $CO_2$/95% air. Human dermal fibroblasts (HOF) and human cholangio-adenocarcinoma cell line (MEC) were used as cells. After culturing the cells for five days, the cells were fixed with formalin and stained directly with hematoxylin-eosin (HE). In the case of MEC, the cells formed several colonies on the collagen hydrogel thin film as shown in the photograph in FIG. 6. In the case of HDF, some cells seemed to invade the collagen hydrogel thin film (photo in FIG. 7). A frozen cross-section of the gel was therefore prepared and subjected to HE staining: while MEC showed no invasion into the gel, HOF revealed an apparent invasion into the gel.

It is needless to mention that the present invention is not limited in any manner by the examples shown above. Various embodiments are possible as to cells capable of being cultured, composition of culture medium, and culturing conditions as well as kinds of an extracellular matrix components such as a collagen hydrogel thin film, composition of substratum, thickness and elastic strength of the thin film.

According to the present invention, as described above in detail, there are available a culture substratum and an organ adhesion preventive substance of a hydrogel thin film containing one or more extracellular matrix components such as collagen, which can be easily prepared and provides an excellent expediency.

What is claimed is:

1. A method of making a hydrated and vitrified matrix gel consisting essentially of one or more extracellular matrix components, which comprises:
   incubating an aqueous solution consisting essentially of one or more extracellular matrix components within a retainer to form a matrix gel in a retainer,
   drying the matrix gel in the retainer to form a vitrified matrix gel in the retainer, and
   hydrating the vitrified matrix gel to make the hydrated and vitrified matrix gel in the retainer.

2. The method according to claim 1, wherein one of the extracellular matrix components is collagen.

3. The method according to claim 1, wherein the retainer is an annulus, a mesh, a cylinder or a container.

4. The method according to claim 1, which consists essentially of:
   incubating an aqueous solution consisting essentially of one or more extracellular matrix components within a retainer to form a matrix gel in a retainer,
   drying the matrix gel in the retainer to form a vitrified matrix gel in the retainer, and
   hydrating the vitrified matrix gel to make the hydrated and vitrified matrix gel in the retainer.

5. A method of making a hydrated and vitrified matrix gel consisting essentially of one or more extracellular matrix components and one or more cell culture medium components, which comprises:
   incubating an aqueous solution consisting essentially of one or more extracellular matrix components and one or more cell culture medium components within a retainer to form a matrix gel in a retainer,
   drying the matrix gel in the retainer to form a vitrified matrix gel in the retainer, and
   hydrating the vitrified matrix gel to make the hydrated and vitrified matrix gel in the retainer.

6. The method according to claim 5, wherein one of the extracellular matrix components is collagen.

7. The method according to claim 5, wherein the retainer is an annulus, a mesh, a cylinder or a container.

8. The method according to claim 5, which consists essentially of:
   incubating an aqueous solution consisting essentially of one or more extracellular matrix components and one or more cell culture medium components within a retainer to form a matrix gel in a retainer,
   drying the matrix gel in the retainer to form a vitrified matrix gel in the retainer, and
   hydrating the vitrified matrix gel to make the hydrated and vitrified matrix gel in the retainer.

* * * * *